United States Patent [19]
Chittum et al.

[11] Patent Number: 5,577,510
[45] Date of Patent: Nov. 26, 1996

[54] PORTABLE AND PROGRAMMABLE BIOFEEDBACK SYSTEM WITH SWITCHING CIRCUIT FOR VOICE-MESSAGE RECORDING AND PLAYBACK

[76] Inventors: William R. Chittum, 1030 Mowere Rd., Phoenixville, Pa. 19460; Martin J. McMorrow, Rte. 2, Box 763, Cobden, Ill. 62920; James M. Baker, Jr., 1101 Collier Rd. NW., B5, Atlanta, Ga. 30318

[21] Appl. No.: 516,743

[22] Filed: Aug. 18, 1995

[51] Int. Cl.$^6$ ............................. A61B 5/04; A61B 5/0432
[52] U.S. Cl. ........................... 128/709; 128/706; 128/710
[58] Field of Search .................................... 628/696, 706, 628/709, 903; 128/696, 706, 709, 903

[56] References Cited

U.S. PATENT DOCUMENTS

| | | | |
|---|---|---|---|
| 4,367,752 | 1/1983 | Jimenez et al. | 128/706 |
| 4,535,783 | 8/1985 | Marangoni | 128/696 |
| 4,583,553 | 4/1986 | Shah et al. | 128/704 |
| 4,788,983 | 12/1988 | Brink et al. | 128/706 |
| 4,889,131 | 12/1989 | Salem et al. | 128/903 |
| 4,938,228 | 7/1990 | Righter et al. | 128/706 |
| 4,981,141 | 1/1991 | Segalowitz | 128/696 |
| 5,228,449 | 7/1993 | Christ et al. | 128/690 |
| 5,245,666 | 9/1993 | Mikell | 381/73.1 |
| 5,285,792 | 2/1994 | Sjoquist et al. | 128/697 |
| 5,299,119 | 3/1994 | Kraf et al. | 128/696 |
| 5,348,008 | 9/1994 | Bornn et al. | 128/696 |
| 5,375,607 | 12/1994 | Sasagawa | 128/706 |

FOREIGN PATENT DOCUMENTS 2922542  4/1980  Germany .................... A61B 5/00

OTHER PUBLICATIONS

"HeartWatch Model 9119: Instruction Manual and Exercise Guide", Computer Instruments Corp., ©1991, pp. 1–10.

Primary Examiner—William E. Kamm
Assistant Examiner—Carl H. Layno
Attorney, Agent, or Firm—Richard C. Litman

[57] ABSTRACT

A portable and programmable biofeedback system which senses a physiological variable, such as heart rate, and both displays the physiological variable in a visual display in real time and activates and deactivates a user prerecorded voice-message upon reaching a user-programmed threshold value for the physiological variable measured. The system is especially useful in the field of behavior modification which require that the patient have reliable access to his or her behavior modification techniques upon onset of the symptoms associated with a diseased behavior. The invention is made up of a combination of components, namely, a bio-signal sensor, a transmitter, a receiver, a processing unit capable of being programmed with a biosignal threshold value and comparing the biosignal to the threshold value, a switching circuit into which an output signal is input, and an analog or digital message recording and playback device operably linked to the switching circuit so that a playback device is activated or deactivated when the output and threshold values match. A display mechanism for visually displaying the real-time changes of the biosignal is linked to the processing unit.

6 Claims, 3 Drawing Sheets

PORTABLE AND PROGRAMMABLE BIOFEEDBACK SYSTEM WITH SWITCHING CIRCUIT FOR VOICE-MESSAGE RECORDING AND PLAYBACK

BACKGROUND OF THE INVENTION

1. Field of the Invention

The present invention relates to a portable and programmable biofeedback system which senses a physiological variable (biosignal), such as heart rate, and both displays the physiological variable in a visual display in real time and activates and deactivates a user prerecorded voice-message upon reaching a user-programmed threshold value for the physiological variable measured.

2. Description of the Prior Art

Biofeedback systems are known in the prior art to be therapeutically useful to monitor and regulate physiological functions and psychological or emotional behavior. Typically, and as is well known in the prior art, various sensory devices are available to translate physiological variables into a visual or an auditory display, thereby allowing a user to monitor the change in values of the physiological variable. Such physiological variables have been measured by various means and include cardiac neuroelectric potentials (electrocardiogram or EKG), muscular neuroelectric potentials (electromyogram or EMG), heart rate (pulse), galvanic skin response (GSR), photoplethysmography (blood vessel enlargement measurement), blood gas values (carbon dioxide and oxygen levels), respiration rate and body temperature. In a biofeedback system, regardless of the variable measured and inputted into the system, the user attempts to adjust those physiological variables in a way which alters the output displayed, thereby learning to control the variable.

Presently, however, a user's control over his or her response to the information displayed and effectiveness in learning therefrom is limited by the type of output or display provided with the biofeedback apparatus. For example, a user may be in need of immediate instruction for modification of a behavioral disorder as a result of an onset, often in public. In other situations, a user may desire or be able to best respond to his or her own created messages, avoiding "burnout" to pre-recorded behavior modification messages. However, the prior art regarding biofeedback devices fails to address the need for a portable, concealable biofeedback apparatus allowing the user to alter the output voice messages to which the user responds and to receive these messages in real-time at the time of a sudden onset.

As found in the prior art, one group of portable units which sense biosignals are dependent upon base units to communicate with a portable user-worn sensing device. The base units then either activate information displays in the base unit or activate intermediate communication means to further translate a signal to a remote site. For example, U.S. Pat. No. 5,375,607 issued Dec. 27, 1994 to Sassagawa discloses a telemeter apparatus for counting a heart rate without being affected by a radio interference between adjacent exercise test systems. The telemeter apparatus has a (1) wireless transmitter unit for transmitting a heart beat signal detected from a subject, (2) receiving coils on each side of a treadmill or similar exercise test system, (3) at least two comparators for accepting and comparing a signal with a predetermined threshold level, (4) an AND circuit to which output signals from the comparators are input, and (5) a heart rate display unit. The comparators, AND circuit and heart rate display all reside in the treadmill.

U.S. Pat. No. 5,228,449 issued Jul. 20, 1993 to Christ et al. describes a wrist worn monitor system and method for detecting out-of-hospital cardiac emergencies and summoning emergency assistance by using a photoplethysmograph to monitor pulse through a wrist-worn unit. The wrist-worn unit communicates by radio frequency with a base unit, which in turn may activate local alarms, an auto-dialer to telephone for help, or other devices to alert rescue authorities. This system is useful in alerting another person that a cardiac event has occurred, but fails to provide voice biofeedback useful to help initially prevent a problem. Both the '607 and '449 patents describe devices that fail to address the purpose of providing a portable and concealable unit for delivering voice messages controlled exclusively by the user.

Another group of both portable and concealable units only provide a very limited audible or visual display of the biosignal sensed, without providing a user input means for changing the output message. For example, the CIC HEARTWATCH™ Instruction Manual and Exercise Guide, copyright 1991, describes a commercially available wrist-worn heart rate monitor with means for setting an alarm for an upper and lower exercise heart rate value and LCD display for displaying the heart rate in real time. Electrodes and a transmitter are housed in a chest belt to sense heart signals. Next, U.S. Pat. No. 4,938,228 issued Jul. 3, 1990 to Righter et al. describes a wrist worn heart rate monitor which is intended to display a user's heart rate with a medical grade accuracy during vigorous physical exercise in an LCD display. German Publication No. 29 22 542 published Apr. 12, 1980, describes a user-worn first-alert system which is able to monitor various physiological signals such as heart rate, respiration rate, blood pressure, body temperature and activate an alarm. It is intended for use in a hospital setting or elderly for individuals living alone. None of the inventions so described are linked with a recording/playback device to activate a voice biofeedback message.

A final group of devices is capable of monitoring and recording a biosignal, but none of these devices correlate the activation and deactivation of a message playback and recording device with a predetermined biosignal threshold value input. U.S. Pat. No. 5,245,666 issued Sep. 14, 1993 to Mikell describes a subliminal messaging system including a wide range linear subliminal modulator, a digital audio recording or playback device, a microphone to pick up sound at the ear, and an earpiece to deliver the subliminal message. The basic system allows the user to push a button to record an affirmative message on an internal digital-analog storage chip. When the record button is released, the message is presented, repeatedly, at the earpiece at a user-adjustable amplitude. The '666 patent describes a portable device for self-recording messages with no switching device for intermittent activation of a biofeedback message based on a biofeedback signal. It is important to note in contrast that the concept of activating a prerecorded message for use at the moment that a physiological threshold value is reached is critical to the usefulness of the present invention.

U.S. Pat. No. 5,299,119 issued to Kraf et al. describes a programmable cardio-respiratory monitoring system for performing medical diagnostic autonomic nervous system tests by monitoring and analyzing the peaks and intervals of EKG signals in relation to breathing and/or posture regimens. Although a means by which automated audio-visual instructions can prompt a patient to perform a particular regimen is noted, the instructions are not recordable by the user and no means for easily changing the message or for simple, portable use is described.

The prior art fails to disclose a portable, concealable recording/playback device combined with a biosignal monitoring device so that when the user's measured biosignal value reaches a predetermined value, a user-recorded message is activated. The user is thus able to immediately attempt to regulate the biosignal and affect it in such a way that the output message is deactivated after dropping below a user pre-programmed threshold value. None of the above referenced inventions and patents, taken either singly or in combination, is seen to describe the instant invention as claimed.

SUMMARY OF THE INVENTION

The present invention relates to a portable and programmable biofeedback system which senses a physiological variable, such as heart rate, and both displays the physiological variable in a visual display in real time and activates and deactivates a user prerecorded voice-message upon reaching a user-programmed threshold value for the physiological variable measured.

The invention is made up of a combination of components, namely, a biosignal sensor, a transmitter, a receiver, a processing unit capable of being programmed with a biosignal threshold value and comparing the biosignal to the threshold value, a switching circuit into which an output signal is input, and an analog or digital message recording and playback device operably linked to the switching circuit so that a playback device is activated or deactivated when the output and threshold values match. The invention further includes a display mechanism linked to the processing unit for visually displaying the real-time changes of the biosignal.

In the preferred embodiment, the invention includes two major components, a wireless body component and a portable message component. The wireless body component further includes the biosignal sensor and a battery operated transmitter unit, which are housed in a chest belt. To measure a user's heart rate, the sensor is placed in contact with the skin of the chest by means of electrodes in communication with the transmitter unit. The entire wireless component can be concealed below a user's clothing. The wireless component sends the heart rate signal to a portable message component.

The portable message component is made up of a housing, containing a receiver linked to a processing unit, for receiving and processing the heart rate signal. The processing unit is capable of being programmed by the user with a biosignal threshold value. The threshold value represents a target point to which the heart rate signal is compared. The processing unit is further linked to an audio message recording/playback device. Through a switching circuit, the message playback device is activated when the heart rate exceeds the threshold value, and deactivated when the heart rate drops below the threshold value. In addition, a display mechanism is linked to the processing unit to continually visually display the changes in the biosignal in real time.

Accordingly, it is an object of the present invention to provide a portable voice-message recording/playback device in combination with a biosignal monitoring device.

It is another object of the present invention to provide a means whereby a biosignal is measured and compared to a threshold value to activate or deactivate a playback device for playing a prerecorded voice message.

It is a further object of the present invention to provide a means whereby a biofeedback message can be recorded and a threshold biosignal value can be set by the user for activation of the message in real time.

Still another object of the present invention is to provide a portable biofeedback device which is wireless for improved concealment and everyday use.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
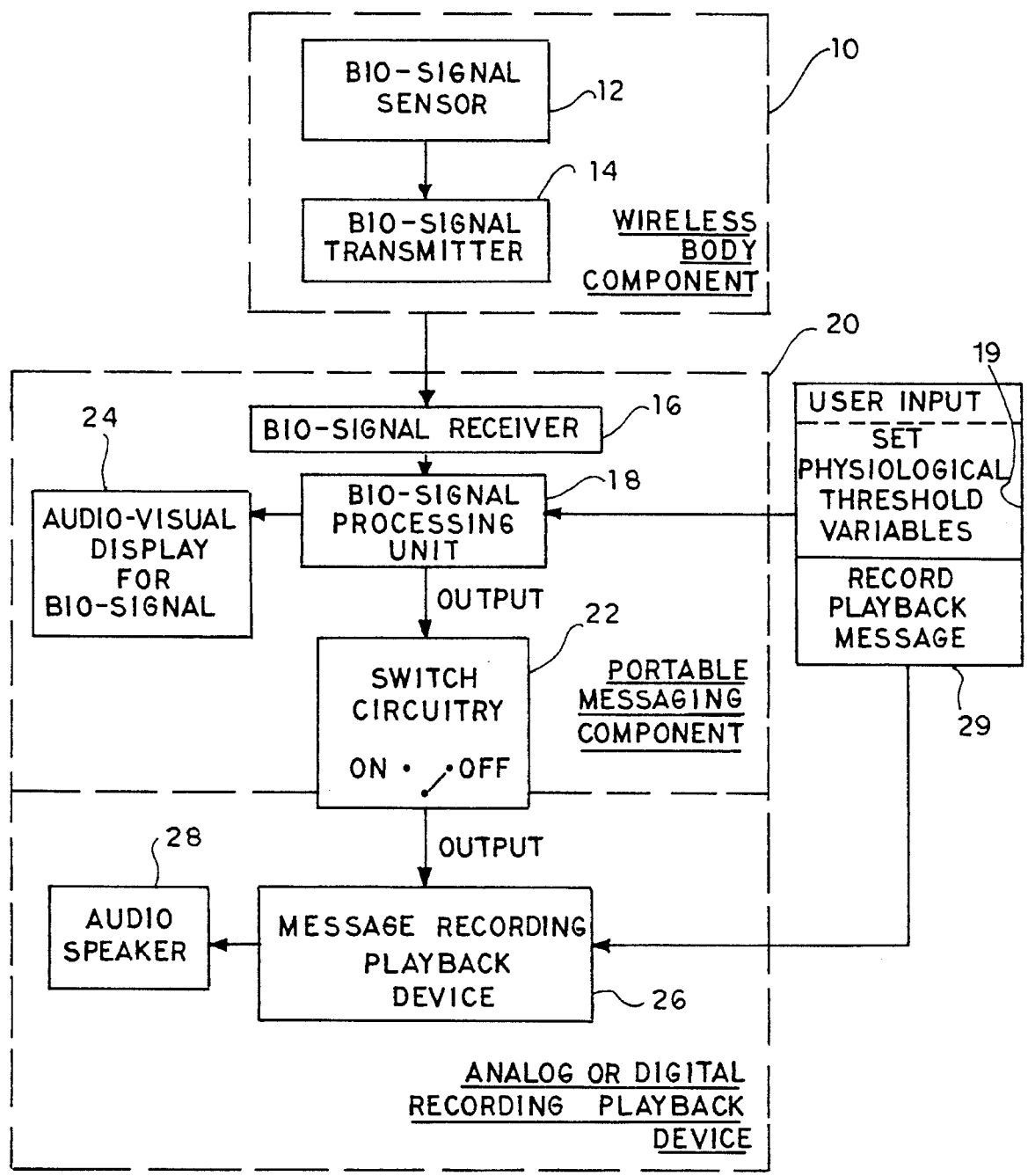
FIG. 1 is a block diagram representing an overview of the components of the system.

In the preferred embodiment of the present invention and referring to FIG. 1 of the drawings, a wireless body component 10 is shown in communication with a portable messaging component 20. A biosignal sensor 12 senses a biosignal which is transmitted by a transmitter 14 to a receiver 16. The receiver 16 is located in the portable messaging component 20 and is operably linked to a processing unit 18. An output signal processed by the processing unit 18 is input both into the switch circuitry 22 and a visual display 24. The visual display 24 may be an LCD display, which continuously and in real time displays a change in the biosignal value processed by the processing unit 18.

The processing unit 18 is also capable of being programmed by a user with a biosignal threshold value, represented by block 19. The switch circuitry 22 is activated when the measured biosignal value reaches the threshold biosignal value. The switching circuit 22 operably links the processing unit 18 to an analog or digital message recording and playback device 26, which is further linked to an audio speaker 28. As represented by block 29, the message recording and playback device is capable of allowing a user to record a message as necessary. The playback portion of the recording playback device 26 is activated when the measured biosignal value equals or exceeds the threshold value. Similarly, a drop in the measured biosignal value below the threshold value deactivates the playback device 26.

Applications for such a device, especially in the field of behavior modification, especially for diseases such as panic disorder, self-abuse, explosive disorder, obsessive-compulsive disorder, pain management, etc., each require that the patient have reliable access to his or her behavior modification techniques upon onset of the symptoms associated with the diseased behavior. Onset may occur under any circumstances, in public, in private, and near or away from home, so a portable device is needed.

Figure 2:
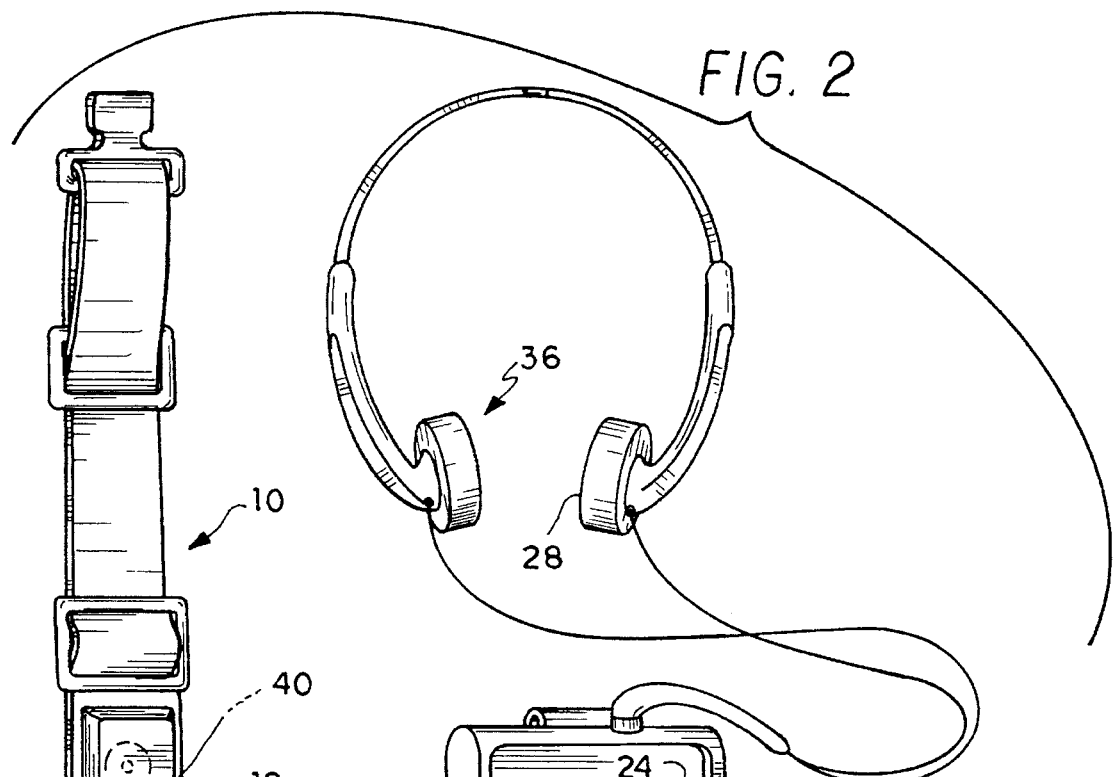
FIG. 2 is an perspective view of the components of the system as embodied for portable use.
Figure 3:
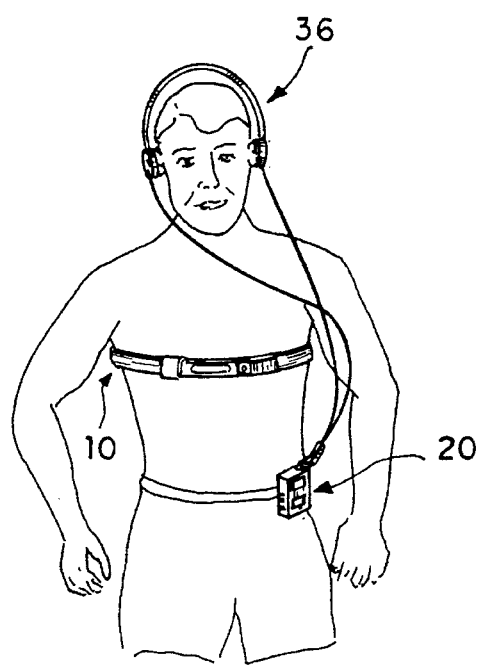
FIG. 3 is an environmental view of the embodiment as shown in FIG. 2 in use.

Therefore, in the preferred embodiment as shown in FIG. 2 and FIG. 3, the wireless body component 10 is made up of the biosignal sensor 12 housed in a portable and concealable chest belt 38. To measure a user's heart rate, electrodes 40 (shown in broken lines as located on the rear side of the belt) are placed in direct contact with the skin of the chest. A device known in the prior art for measuring and visually and audibly displaying a heart rate is the CIC HEART-WATCH™, model 9119, which can be modified and incorporated into the preferred embodiment. The CIC HEART-WATCH™ uses a wireless body component which when worn on the chest can be concealed below a user's clothing and transmits a signal to a wrist-watch component for display. The wireless body component of the CIC HEART-WATCH™ is suitable for use unmodified in the preferred embodiment of the present invention. However, it should be noted that depending on the biosignal to be measured, a biosignal sensor 12 suitable to the measured biosignal should be employed instead of a heart rate monitor. Suitable devices may include, for example, EMG monitors, EEG monitors, photoplethysmograph monitors, body temperature monitors, and respiration monitors.

The wireless body component 10 sends the heart rate signal to the portable messaging component 20, which may be practically and unobtrusively used under a variety of circumstances. For example and as shown in FIG. 3, the portable messaging component 20 can be worn on the belt of an individual and has the look and function of a portable, battery powered audio cassette tape recorder.

In the preferred embodiment, a tape recorder 32 is modified to be automatically activated by the switch circuitry 22 (not shown in FIG. 2) when the switch circuitry is on; when the switch circuitry is off, the tape recorder 32 is able to record and play back messages unaffected by output from the processing unit 18. The processing unit 18 and switch circuitry 22 are built into the housing 42 of the tape recorder 32. The processing unit 18 is also operably linked to the visual display 24 which can be inconspicuously built into the housing 42 for viewing of the biosignal value. Programming buttons 34 by which the user sets the threshold biosignal are shown below the display 24, which allow programming of the biosignal threshold value into the processing unit 18. Headphones 36, as commonly used with audio tape recorders, may be used so that it would appear to the casual observer that the individual is merely using an ordinary cassette player when an audio speaker 28 has been activated.

Figure 4:
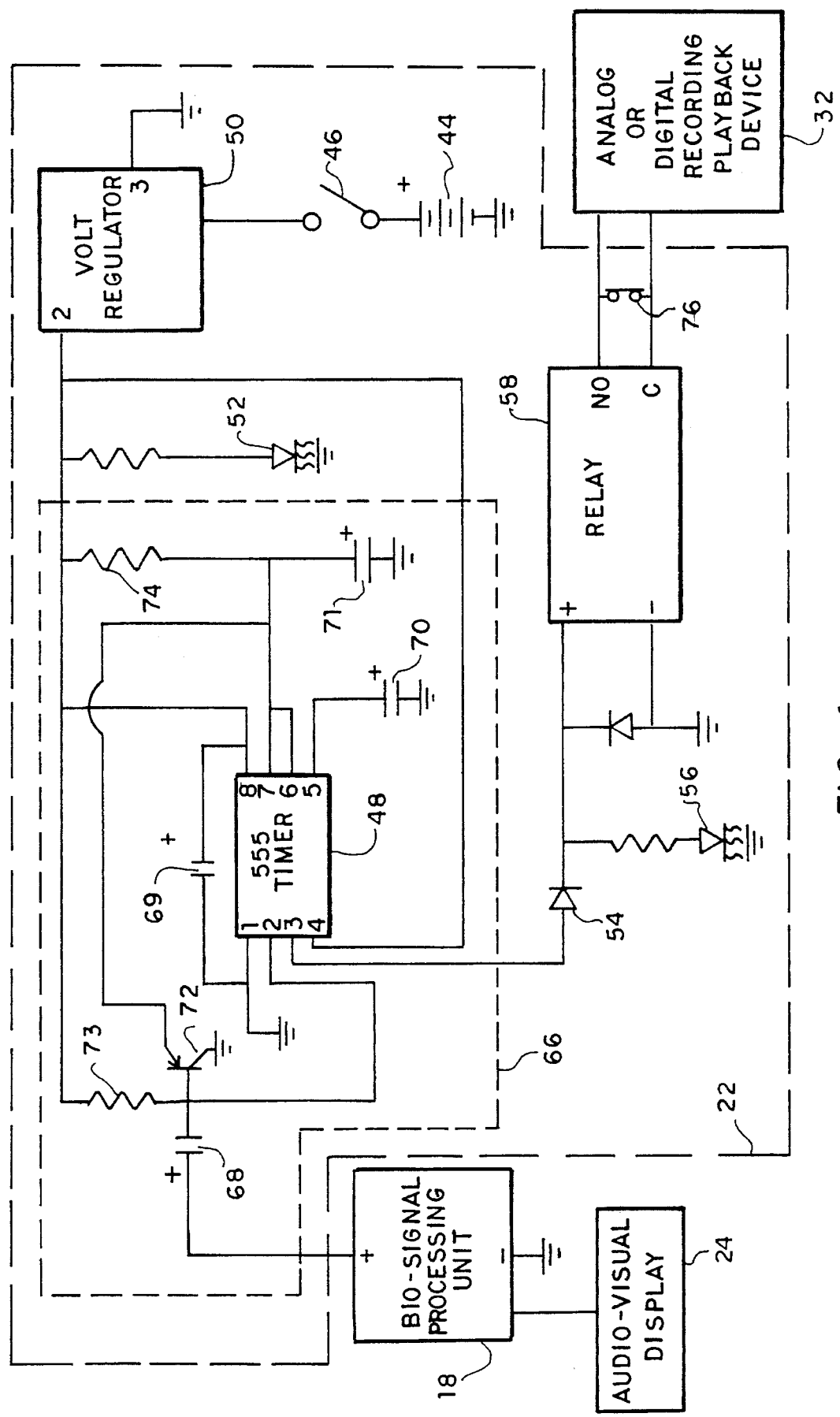
FIG. 4 is a schematic diagram of the switch circuitry block in accordance with the embodiment as shown in FIG. 2.

Referring now to FIG. 4, a schematic diagram of the switch circuitry 22 is shown, necessary for the activation of a recording and playback device 32 when using a prior art processing unit which emits an oscillating pulse, namely, the receiver and programmable processing unit of the CIC HEARTWATCH™. The commercially available CIC HEARTWATCH™ component requires modification by incorporation of a retriggering circuit capable of producing a 5-volt high logic signal to activate the recording playback device 32 as used in the embodiment shown in FIG. 2. However, it should be noted that, although a switching circuit is necessary to activate and deactivate a recording playback device dependent upon a measured biosignal, the specific circuitry used in the present invention will depend upon the type of output signal produced by the receiver/processor unit.

In the preferred embodiment and shown in the schematic of FIG. 4, the biosignal presented as the measured value of heart rate is received by the processing unit be. The processing unit 18 compares the heart rate signal to the threshold value set by the user and sends an oscillating output from the positive terminal when the heart rate signal exceeds the threshold value. The visual biosignal display 24 is also shown peripheral to the switch circuitry 22, independently displaying the real time changes of the biosignal output from the processing unit be. The oscillating output at the positive terminal is input to the switch circuitry 22.

The switch circuitry 22 is powered by a 9-volt battery 44 connected to an on/off switch 46. The on/off switch 46, when in the open position (off mode), allows a battery operated tape recorder 32 to be operated independently of the processing unit 18; when closed, the switch 46 allows voltage to pass through a 7808 8-volt regulator 50 to power the circuit. A light emitting diode at 52 is activated to indicate that the switch circuitry 22 is powered.

Block 66, comprising of capacitors 68, 69, 70 and 71, transistor 72, resistors 73 and 74, and a 555 timer 48, represents the circuit necessary to convert the oscillating pulse to a single high logic output. The 555 timer 48 provides means by which a suitable time delay, such as 15 seconds, is integrated into the circuit to prevent irregular activation and deactivation of the tape recorder 32 when the biosignal bounces above and below the threshold value set. The time delay allows a voltage to be maintained to continue activation of the tape recorder 32 until such time that the processing unit has continuously failed to send the oscillating pulse over the period of the delay. The resulting high logic output voltage is generated from pin 3 of the 555 timer 48, passes through a diode 54, activates a light emitting diode 56 which indicates that high logic output is present, and is directed to the positive terminal of the normally open relay 58.

The tape recorder 32 is shown peripherally connected to the switch circuitry 22. A closed switch 76 represents that the circuit in the tape recorder 32 must be closed to be activated when the on/off switch 46 is in the on mode and oscillating output is present. The high logic output directed to the normally open relay switch 58 causes the relay switch to close and automatically activate the tape recorder 32 when voltage is supplied to the positive terminal. When voltage is removed, the relay returns to its normally open (NO) position to deactivate the tape recorder 32.

It is to be understood that the present invention is not limited to the embodiments described above, but encompasses any and all embodiments within the scope of the following claims.

We claim:

1. A biofeedback system for recording a message, monitoring a physiological signal and triggering the message upon sensing a predetermined value of the physiological signal, comprising:

a first component including a sensing means for measuring a physiological signal, said sensing means adapted to be worn in contact with the body of a user and portable; and a second component including
voice-message delivery means for delivering a prerecorded voice-message;
voice-message recording means operably linked with said voice-message delivery means for recording said prerecorded voice-message;
processing means operably linked with said sensing means and said voice-message delivery means;
input means manually operable by the user capable of causing a physiological signal threshold value to be set in said processing means;
wherein said processing means includes (a) means to process the physiological signal and to produce a first electronic output conveying the physiological signal measured in real time, (b) means to compare a physiological signal value with said threshold value, (c) means to produce a second output when said physiological signal value equals or exceeds said threshold value, (d) means to terminate said second output when said physiological signal value drops below said threshold value; and, switch circuitry for receiving said second output and automatically activating and deactivating said voice-message delivery means, wherein said switch circuitry includes a battery operably linked to a switch, said switch having an off mode and an on mode, said switch being operably linked to said voice-message delivery means such that when said switch is in said off mode said battery permits voltage to pass through said voice-message delivery means to allow use of said voice-message delivery means independently from said processing means.

2. The biofeedback system according to claim 1 wherein said second component further includes visual display means for receiving said first electronic output and displaying the physiological signal in real time, operably linked to said processing means.

3. The biofeedback system according to claim 1 wherein said first component further includes a wireless transmitter operably linked to said sensing means for sending a communications signal carrying the physiological signal information and adapted to be worn by a user remotely from said second component, said second component further including a receiver for receiving said communications signal operably linked to said processor unit.

4. A biofeedback system for recording a message, monitoring a heart rate signal and triggering the message upon sensing a predetermined value of the heart rate signal, comprising:

a wireless body component including a sensing means for measuring a heart rate signal, said sensing means including electrodes capable of being worn by a user in contact with the body, said sensing means in communication with a transmitter capable of sending a communications signal; and a portable messaging component including
a housing;
voice-message delivery means housed within said housing, said voice-message delivery means for delivering a prerecorded voice-message;
voice-message recording means housed within said housing, said voice-message recording means operably linked with said voice-message delivery means for recording said prerecorded voice-message;
a receiver housed within said housing, said receiver for receiving said communications signal;
processing means housed within said housing, said processing means operably linked with said receiver and said voice-message delivery means;
input means housed within said housing, said input means manually operable by the user capable of causing a physiological signal threshold value to be set in said portable messaging component, said input means operably linked to said processing means;
wherein said processing means includes (a) means to process the communications signal and to produce a first electronic output conveying the heart rate signal measured in real time, (b) means to compare a heart rate signal value with said threshold value, (c) means to produce a second output when said heart rate signal value equals or exceeds said threshold value, and (d) means to terminate said second output when said heart rate signal value drops below said threshold value;
visual display means housed within said housing, said visual display means for receiving said first electronic output and displaying the heart rate signal value in real time, operably linked to said processing means; and
switch circuitry housed within said housing, said switch circuitry for receiving said second output and automatically activating and deactivating said voice-message delivery means, wherein said switch circuitry includes a battery operably linked to a switch, said switch having an off mode and an on mode, said switch being operably linked to said voice-message delivery means such that when said switch is in said off mode said battery permits voltage to pass through said voice-message delivery means to allow use of said voice-message delivery means independently from said processing means.

5. The biofeedback system according to claim 4 wherein said wireless body component further includes a belt adapted for wearing around the chest and housing said sensing means and transmitter.

6. The biofeedback system according to claim 4 wherein said second electronic output is an oscillating output and wherein said switch circuitry includes a plurality of capacitors, a transistor, a plurality of resistors, and a timer operably linked together for converting said oscillating output to a high logic output.

* * * * *